(12) United States Patent
Zhu et al.

(10) Patent No.: US 7,829,719 B2
(45) Date of Patent: *Nov. 9, 2010

(54) INSECTICIDAL N-SUBSTITUTED SULFOXIMINES

(75) Inventors: Yuanming Zhu, Carmel, IN (US); Richard B. Rogers, Mobile, AL (US); Jim X. Huang, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/616,383

(22) Filed: Nov. 11, 2009

(65) Prior Publication Data

US 2010/0056579 A1   Mar. 4, 2010

Related U.S. Application Data

(62) Division of application No. 11/101,924, filed on Apr. 8, 2005, now Pat. No. 7,678,920.

(60) Provisional application No. 60/560,628, filed on Apr. 8, 2004.

(51) Int. Cl.
C07D 409/00 (2006.01)
C07D 277/20 (2006.01)
C07D 261/06 (2006.01)
A61K 31/44 (2006.01)

(52) U.S. Cl. .................. 546/280.4; 548/202; 548/247; 514/336; 514/340

(58) Field of Classification Search ............. 546/280.4; 548/202, 247; 514/336, 340
See application file for complete search history.

(56) References Cited

U.S. PATENT DOCUMENTS

| | | | |
|---|---|---|---|
| 3,711,486 A | 1/1973 | Torba et al. | |
| 3,787,420 A | 1/1974 | Torba et al. | |
| 3,852,279 A | 12/1974 | Krapcho et al. | |
| 4,577,028 A | 3/1986 | Martin et al. | |
| 4,692,184 A | 9/1987 | Lee | |
| 4,747,871 A | 5/1988 | Ruminski et al. | |
| 4,833,158 A | 5/1989 | Twydell et al. | |
| 4,948,896 A | 8/1990 | Nagao | |
| 4,973,695 A | 11/1990 | Yamashita et al. | |
| 5,053,516 A | 10/1991 | Hartmann et al. | |
| 5,099,023 A | 3/1992 | Miller et al. | |
| 5,099,024 A | 3/1992 | Pulwer et al. | |
| 5,118,809 A | 6/1992 | Cevasco et al. | |
| 5,124,458 A | 6/1992 | Cevasco et al. | |
| 5,169,432 A | 12/1992 | Auinbauh et al. | |
| 5,225,560 A | 7/1993 | Cevasco et al. | |
| 5,227,491 A | 7/1993 | Doehner, Jr. | |
| 5,229,519 A | 7/1993 | Zhang et al. | |
| 6,060,502 A | 5/2000 | Louder et al. | |
| 7,795,456 B2 * | 9/2010 | Zhu et al. | 549/69 |
| 2003/0078430 A1 | 4/2003 | Satake et al. | |
| 2004/0158067 A1 | 8/2004 | Hutchinson et al. | |
| 2006/0199964 A1 | 9/2006 | Jackson et al. | |
| 2007/0249837 A1 | 10/2007 | Gebhardt et al. | |
| 2010/0056578 A1 * | 3/2010 | Zhu et al. | 514/336 |

FOREIGN PATENT DOCUMENTS

| | | |
|---|---|---|
| DE | 19523658 A1 | 6/1995 |
| GB | 1307271 | 2/1973 |
| WO | 96/39389 | 12/1996 |
| WO | WO98/02492 | 1/1998 |

* cited by examiner

Primary Examiner—Rita J Desai
Assistant Examiner—John Mabry
(74) Attorney, Agent, or Firm—Carl D. Corvin; Craig E. Mixan

(57) ABSTRACT

N-Substituted sulfoximines are effective at controlling insects.

4 Claims, No Drawings

INSECTICIDAL N-SUBSTITUTED SULFOXIMINES

CROSS-REFERENCE TO RELATED APPLICATION

This application is a divisional of U.S. non-provisional application Ser. No. 11/101,924 filed on 8 Apr. 2005, which claims priority from U.S. provisional application 60/560,628 filed on 8 Apr. 2004. The disclosures of application Ser. No. 11/101,924 and 60/560,628 are hereby incorporated, in their entirety, by reference.

BACKGROUND OF THE INVENTION

The present invention concerns novel N-substituted sulfoximines and their use in controlling insects, particularly aphids. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

SUMMARY OF THE INVENTION

This invention concerns compounds useful for the control of insects, especially useful for the control of aphids and other sucking insects. More specifically, the invention concerns compounds of the formula (I)

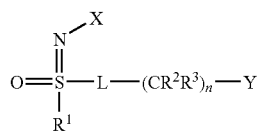

(I)

wherein
X represents $NO_2$, CN or $COOR^4$;
L represents a single bond or $R^1$, S and L taken together represent a 5- or 6-membered ring;
$R^1$ represents methyl or ethyl;
$R^2$ and $R^3$ independently represent hydrogen, methyl, ethyl, fluoro, chloro or bromo;
n is an integer from 0-3;
Y represents 6-halopyridin-3-yl, 6-($C_1$-$C_4$)alkylpyridin-3-yl, 6-($C_1$-$C_4$)alkoxypyridin-3-yl, 2-chlorothiazol-4-yl, or 3-chloroisoxazol-5-yl when n=0-3 and L represents a single bond, or Y represents hydrogen, $C_1$-$C_4$ alkyl, phenyl, 6-halopyridin-3-yl, 6-($C_1$-$C_4$)alkylpyridin-3-yl, 6-($C_1$-$C_4$) alkoxypyridin-3-yl, 2-chlorothiazol-4-yl, or 3-chloroisoxazol-5-yl when n=0-1 and $R^1$, S and L taken together represent a 5- or 6-membered ring; and
$R^4$ represents $C_1$-$C_3$ alkyl.

Preferred compounds of formula (I) include the following classes:

(1) Compounds of formula (I) wherein X is $NO_2$ or CN, most preferably CN.

(2) Compounds of formula (I) wherein $R^1$, S and L taken together form a standard 5-membered ring, n=1, and Y represents 6-chloropyridin-3-yl, i.e., having the structure

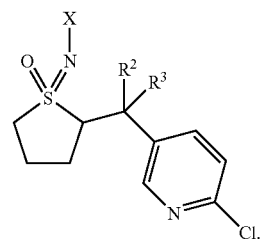

(3) Compounds of formula (I) wherein $R^1$, S and L taken together form a standard 5-membered ring and n=0, i.e., having the structure

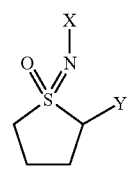

(4) Compounds of formula (I) wherein $R^1$ represents $CH_3$, L represents a single bond and Y represents 6-chloropyridin-3-yl, i.e., having the structure

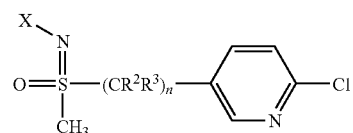

wherein n=1-3.

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the term alkyl (including derivative terms such as alkoxy) as used herein include straight chain, branched chain, and cyclic groups. Thus, typical alkyl groups are methyl, ethyl, 1-methylethyl, propyl, 1,1-dimethylethyl, and cyclopropyl. The term halogen includes fluorine, chlorine, bromine, and iodine.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (Ia), wherein $R^1$, $R^2$, $R^3$, $R^4$, X, and Y are as previously defined and L is a single bond, can be prepared by the methods illustrated in Scheme A:

Scheme A

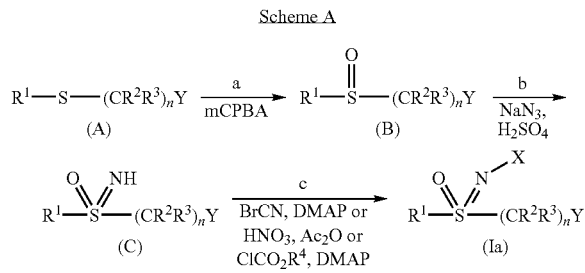

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl ($R^4$) chloroformate in the presence of base such as 4-dimethylaminopyridine (DMAP) to provide N-substituted sulfoximine (Ia). Base is required for efficient cyanation and carboxylation and the preferred base is DMAP, whereas sulfuric acid is used as catalyst for efficient nitration reaction.

The compounds of formula (Ia), wherein X represents CN and $R^1$, $R^2$, $R^3$, $R^4$ and Y are as previously defined, can be prepared by the mild and efficient method illustrated in Scheme B.

Scheme B

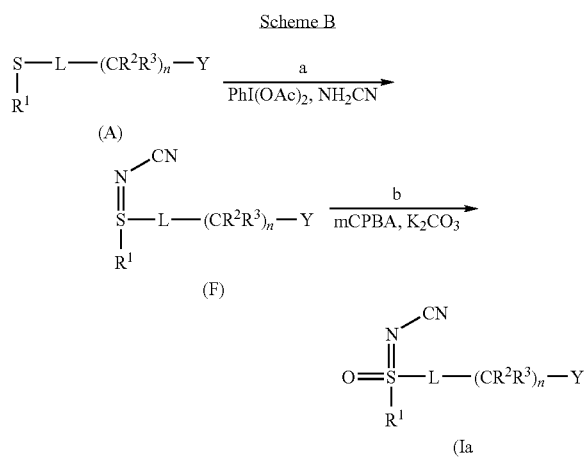

In step a of Scheme B, sulfide is oxidized with iodobenzene diacetate in the presence of cyanamide at 0° C. to give sulfilimine (F). The reaction can be carried out in a polar aprotic solvent like $CH_2Cl_2$.

In step b of Scheme B, the sulfilimine (F) is oxidized with mCPBA. A base such as potassium carbonate is employed to neutralize the acidity of mCPBA. Protic polar solvents such as ethanol and water are used to increase the solubility of the sulfilimine starting material and the base employed.

The α-carbon of the N-substituted sulfoximine of formula (Ia), i.e., n=1, $R^3$=H in the ($CR^2R^3$) group adjacent to the N-substituted sulfoximine function can be further alkylated or halogenated ($R^5$) in the presence of a base such as potassium hexamethyldisilamide (KHMDS) to give N-substituted sulfoximines of formula (Ib), wherein $R^1$, $R^2$, $R^3$, $R^4$, X, L and Y are as previously defined and Z is an appropriate leaving group, as illustrated in Scheme C. The preferred leaving groups are iodide ($R^5$=alkyl), benzenesulfonimide ($R^5$=F), tetrachloroethene ($R^5$=Cl), and tetrafluoroethene ($R^5$=Br).

Scheme C

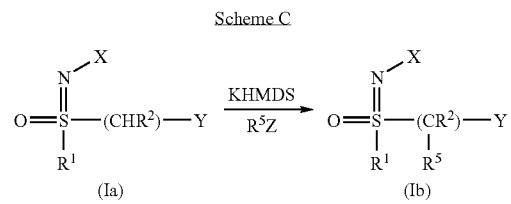

The starting sulfides (A) in Scheme A can be prepared in different ways as illustrated in Schemes D, E, F G and H.

In Scheme D, the sulfide of formula ($A_1$), wherein $R^1$, $R^2$ and Y are as previously defined and $R^3$=H, can be prepared from the chloride of formula ($D_1$) by nucleophilic substitution with the sodium salt of an alkyl thiol.

Scheme D

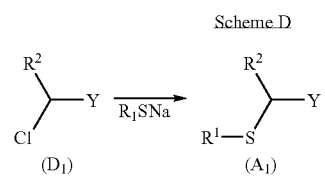

In Scheme E, the sulfide of formula ($A_2$), wherein $R^1$, $R^2$ and Y are as previously defined and $R^3$=H, can be prepared from the chloride of formula ($D_2$) by reacting with a 2-mono substituted methyl malonate in the presence of base such as potassium tert-butoxide to provide 2,2-disubstituted malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme E

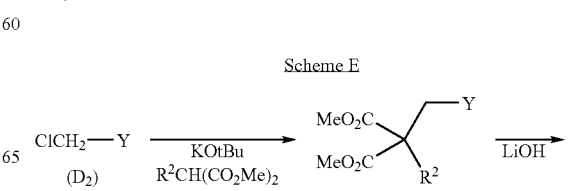

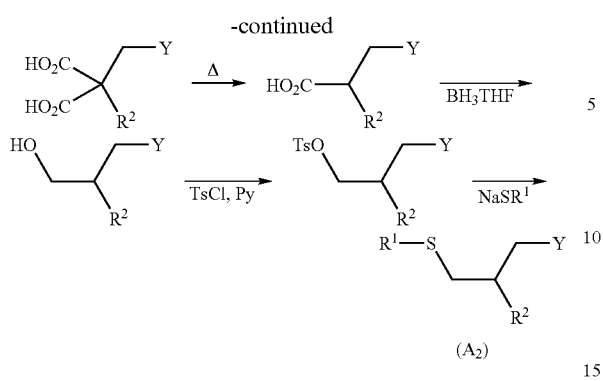

(A₂)

In Scheme F, the sulfide of formula (A₃), wherein $R^1$, $R^2$ and Y are as previously defined and $R^3$=H, can be prepared from the nitrile of formula (E) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

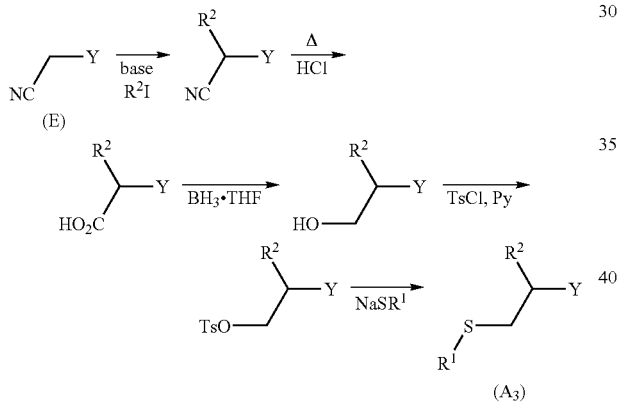

In Scheme G, the sulfide of formula (A₄), wherein $R^1$, S and L taken together form a ring, n=0, Y=isopropyl or phenyl can be prepared from the unsubstituted cyclic sulfide wherein m=0, 1. Chlorination of the cyclic sulfide starting material with N-chlorosuccinimide in benzene followed by alkylation with Grignard reagent can lead to the desired sulfide (A₄) in satisfactory yield.

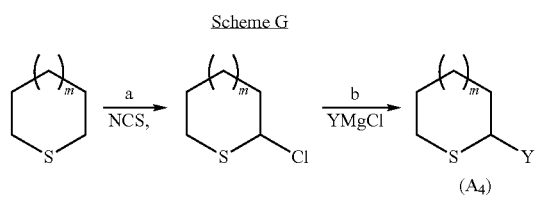

In Scheme H, the sulfide of formula (A₅), wherein $R^1$ is previously defined, L is a bond, n is 0 and Y is 6-chloropyridin-3-yl can be prepared from 2-chloro-5-bromopyridine with a halo-metal exchange followed by a substitution with disulfide.

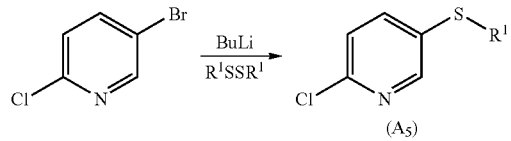

Sulfoximine compounds wherein $R^1$, S and L taken together form a saturated 5- or 6-membered ring can also be prepared by the methods illustrated in Scheme I wherein X and Y are as previously defined and m is 0 or 1.

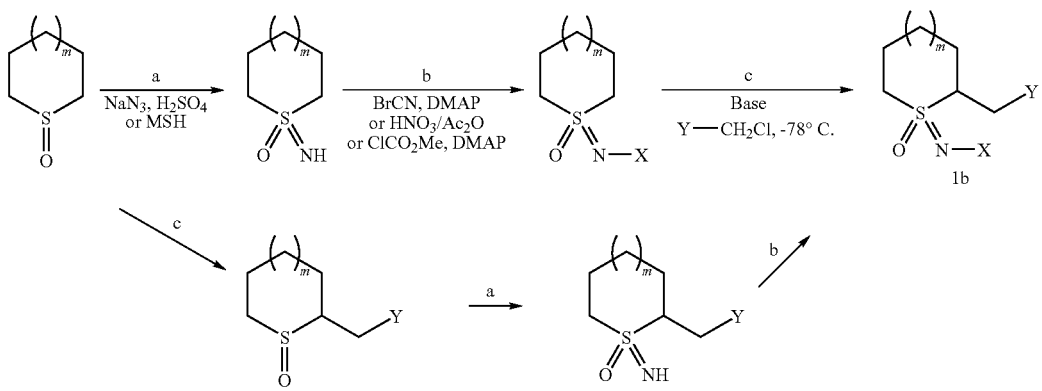

In step a of Scheme I, which is similar to step b of Scheme A, sulfoxide is iminated with sodium azide in the presence of concentrated sulfuric acid or with O-mesitylsulfonylhydroxylamine in a polar aprotic solvent to provide sulfoximine. Chloroform or dichloromethane are the preferred solvents.

In step b of Scheme I, similar to step c of Scheme A, the nitrogen of sulfoximine can be either cyanated with cyanogen bromide, or nitrated with nitric acid followed by treatment with acetic anhydride under refluxing conditions, or carboxylated with methyl chloroformate in the presence of base such as DMAP to provide N-substituted cyclic sulfoximine Base is required for efficient cyanation and carboxylation and the preferred base is DMAP, whereas sulfuric acid is used as catalyst for efficient nitration reaction.

In step c of Scheme I, the α-carbon of N-substituted sulfoximine can be alkylated with a heteroaromatic methyl halide in the presence of a base such as KHMDS or butyl lithium (BuLi) to give the desired N-substituted sulfoximines. The preferred halide can be bromide, chloride or iodide.

Alternatively, the compounds of formula (Ib) can be prepared by a first α-alkylation of sulfoxides to give α-substituted sulfoxides and then an imination of the sulfoxide followed by N-substitution of the resulting sulfoximine by using the steps c, a and b respectively as described above for Scheme I.

EXAMPLES

Examples I-X Preparation of N-Substituted Sulfoximines

Example I

[3-(6-Chloropyridin-3-yl)-2-methylpropyl](methyl) oxido-λ⁴-sulfanylidenecyanamide (2)

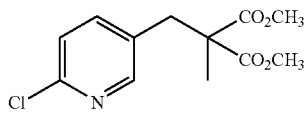

2

A) Dimethyl 2-[(6-chloropyridin-3-yl)methyl]-2-methylmalonate

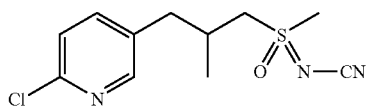

To a stirred solution of potassium tert-butoxide (4.49 g, 40 mmol) in tetrahydrofuran (THF, 100 mL) was added dimethyl methylmalonate (6.43 g, 44 mmol) dropwise at room temperature. After 10 min, 3-chloromethyl-6-chloropyridine (6.48 g, 40 mmol) was added and the resulting mixture was stirred at room temperature overnight. The mixture was poured into water (400 mL) and then extracted with ether (2×150 mL). The organic fractions were combined, washed with brine (100 mL) and dried over anhydrous MgSO₄. The solvent was evaporated to give a yellow oil, which was triturated with boiling hexane (2×100 mL) with the hexane being decanted from insoluble oil. The hexane fractions were combined and cooled to give 6.3 g of the desired malonate derivative as a white solid in 58% yield: m.p. 80-81° C.

B) 2-[6-Chloropyridin-3-yl)methyl]-2-methylmalonic acid

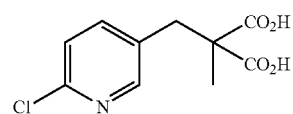

To a stirred solution of dimethyl 2-[(6-chloropyridin-3-yl) methyl]-2-methylmalonate (10.85 g, 40 mmol) in THF (80 mL) was added a solution of lithium hydroxide monohydrate (5.7 g, 0.136 mol) in water (43 mL). The resulting mixture was stirred overnight at room temperature and then poured into water (300 mL). The pH was adjusted to less than 2 by the addition of concentrated HCl. The resulting mixture was extracted with ether (3×100 mL) and the ether extracts were combined, washed with brine (100 mL) and dried over anhydrous MgSO₄. After a filtration, the solvent was evaporated to give 9.26 g of the product as a white solid in 95% yield: m.p. 168° C. (decomp.).

C) 3-(6-Chloropyridin-3-yl)-2-methylpropanoic acid

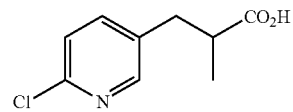

The solid 2-[6-chloropyridin-3-yl)methyl]-2-methylmalonic acid (8.70 g, 37.5 mmol) in a 500 mL round bottom flask was immersed in an oil bath heated to 185° C. As the solid melted carbon dioxide evolution occurred. After heating for 30 min, the reaction was deemed complete. Upon cooling there was obtained an amber gum (6.8 g, 95% yield). [M+H]⁺=200, 202; IR: 1703 (C=O). The product was about 85% pure and was used for the next step reaction directly.

D) 3-(6-Chloropyridin-3-yl)-2-methylpropan-1-ol

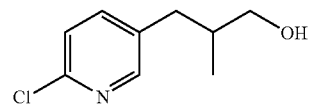

To a stirred solution of 3-(6-chloropyridin-3-yl)-2-methyl-propanoic acid (6.5 g, 32.6 mmol) in THF (75 mL) cooled in an ice-water bath was added a solution of 1 M borane in THF (48 mL, 48 mmol) in a rapid dropwise fashion. The mixture was stirred at room temperature for 4 h. Water (25 mL) was added carefully followed by 2 N NaOH solution. The two phases were separated and the aqueous phase washed with ether (100 mL). The organic phases were combined, dried over anhydrous MgSO₄, filtered, and concentrated to give 4.2 g of the product as a nearly colorless oil in 69% crude yield. [M+H]⁺=186, 188; IR: 3414 (OH)

E) 3-(6-Chloropyridin-3-yl)-2-methylpropyl-4-methylbenzenesulfonate

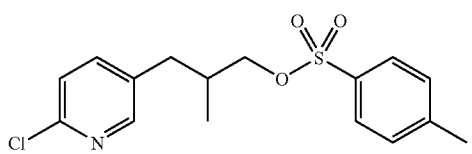

To a stirred solution of 3-(6-chloropyridin-3-yl)-2-methylpropan-1-ol (4.0 g, 21.5 mmol) and pyridine (3.40 g, 43 mmol) in CHCl₃ (30 mL) cooled below 5° C. in an ice-water bath was added p-toluenesulfonyl chloride (6.16 g, 32.3 mmol) in one portion. After 20 min, the ice-water bath was removed and the mixture was continued to stir at room temperature overnight. The solution was then diluted with CH₂Cl₂ (30 mL), washed with 1 N HCl (50 mL), water (50 mL), brine (50 mL), and dried over anhydrous MgSO₄. The solvent was filtered and evaporated to give 9.0 g of the crude product as a yellow oil, which was purified on silica gel using 15% acetone in hexane (v/v) as eluent to give 5.45 g of the desired tosylate product as a colorless oil in 74.6% yield. [M+H]⁺=340, 342; IR: 1177 (S=O).

F) 2-Chloro-5-[2-methyl-3-(methylthio)propyl]pyridine

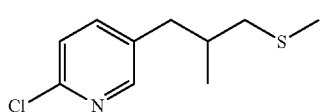

A solution 3-(6-chloropyridin-3-yl)-2-methylpropyl-4-methylbenzenesulfonate (5.0 g, 14.7 mmol) and sodium methylthiolate (2.10 g, 30 mmol) in THF (50 mL) was stirred overnight at room temperature. The remaining unreacted starting material indicated on TLC was converted into the product completely after the solution was heated at 55° C. for 4 more hours. The mixture was diluted with ether and washed with 2 N NaOH solution (50 mL). The aqueous phase was washed with ether (50 mL). The combined organic phase was washed with brine (50 mL), dried over MgSO₄, filtered and concentrated to give 2.94 g of the desired crude sulfide in 93% yield as a yellowish oil: M⁺=215, 217; δ 2.07 (s, 3H), 0.95 (d, 3H).

G) 2-Chloro-5-[2-methyl-3-(methylsulfinyl)propyl]pyridine

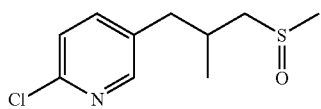

To a stirred solution of 2-chloro-5-[2-methyl-3-(methylthio)propyl]-pyridine (2.60 g, 12.5 mmol) in CH₂Cl₂ (35 mL) cooled to −15° C. in an ice-salt bath was added m-chloroperoxybenzoic acid (mCPBA, ~85%, 2.54 g, ~12.5 mmol) portion wise at such a rate that the temperature never rose above −10° C. After the addition was over, TLC showed that a single product plus a small amount of starting material was present in the solution. To avoid any sulfone formation, the reaction was quenched at this point by the addition of saturated NaHCO₃ (50 mL). The organic layer was separated and the aqueous phase washed with CH₂Cl₂ (25 mL). The combined organic layers were dried over MgSO₄ and the solvent was evaporated to give 2.66 g of crude product as a yellow oil. The oil was triturated with hot hexane (50 mL) and the hexane decanted after cooling. This procedure removed most of the starting material and the resulting product (a mixture of two diastereomers) was directly used for the following step without further purification. [M+H]⁺=232, 234; δ 1.09 (overlapping d, 3H), 2.57, 2.59 (2 s, 3H).

H) 2-Chloro-5-[2-methyl-3-(methylsulfonimidoyl)propyl]pyridine

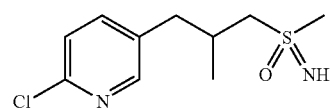

To a stirred mixture of 2-chloro-5-[2-methyl-3-(methylsulfinyl)propyl]-pyridine (2.15 g, 9.3 mmol) and sodium azide (1.81 g, 28 mmol) in chloroform (30 mL) cooled in an ice-water bath was added concentrated H₂SO₄ (6 mL) and the resulting mixture stirred at this temperature for 10 min. The reaction was then heated at 55° C. in an oil-bath for 16 hrs. Upon cooling down, the mixture was diluted with ice-water (70 mL) and the organic layer removed. The aqueous phase was washed with CH₂Cl₂ (2×30 mL) and the organic phase was discarded. The aqueous phase was made basic by the careful addition of aqueous ammonia whereupon an oil separated, which was extracted with CH₂Cl₂ (2×30 mL). The combined organic phase was dried over MgSO₄ and solvent evaporated to give 2.15 g of the product as a yellowish oil in 94% yield. [M+H]⁺=247, 249; δ 1.11 (overlapping d, 3H).

I) [3-(6-Chloropyridin-3-yl)-2-methylpropyl](methyl)oxido-λ⁴-sulfanylidenecyanamide (2)

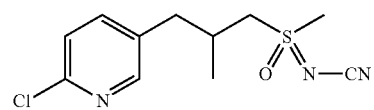

2

To a stirred solution of 2-chloro-5-[2-methyl-3-(methylsulfonimidoyl)-propyl]pyridine (0.432 g, 1.75 mmol) and DMAP (0.24 g, 2 mmol) in CH₂Cl₂ (10 mL) was added a 3 M cyanogen bromide solution in CH₂Cl₂ (1.2 mL, 3.5 mmol) in one portion. There was an immediate exothermic reaction accompanied by gas evolution. After stirring for 30 min at room temperature, TLC showed that all of the starting material had been consumed and replaced by a single product. The reaction mixture was added to the top of a small pad of silica gel and then washed off using 7:3 hexane-acetone (v/v). Removal of the solvent gave 0.39 g of the desired N-cyanosulfoximine (2) as a colorless oil in 82% yield. [M+H]⁺=272, 274; IR: 2189 cm⁻¹.

Example II

Preparation of 2-chloro-5-(2-methyl-3-{methyl (oxido)[oxido-(oxo)hydrazono]-λ⁴-sulfanyl}propyl) pyridine (3)

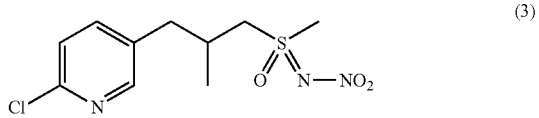

(3)

To a stirred solution of 2-chloro-5-[2-methyl-3-(methylsulfonimidoyl)-propyl]pyridine (0.432 g, 1.75 mmol) (Example I-H) in $CH_2Cl_2$ (10 mL) cooled in an ice-water bath was added 98% $HNO_3$ (0.11 g, 1.75 mmol). The nitrate salt of sulfoximine separated from the solution. To this mixture was added acetic anhydride (4 mL) and a catalytic amount of concentrated $H_2SO_4$ (3 drops). The resulting mixture was stirred at 0° C. for a few minutes and then heated under reflux for 1 h. During this period, the reaction mixture became homogeneous. To the resulting solution was added additional $CH_2Cl_2$ (20 mL) followed by 1 N NaOH (75 mL) and the stirring was continued to quench the acetic anhydride. The organic layer was then separated and the aqueous layer was washed with $CH_2Cl_2$ (80 mL). The combined organic phase was dried over $MgSO_4$ and solvent evaporated to give 0.49 g of product (3) (yellow oil) as a 1:1 mixture of diastereomers in 96% yield. $[M+H]^+=292, 294$.

Example III

2-Chloro-5-(1-methyl-2-{methyl(oxido)[oxido(oxo) hydrazono]-λ⁴-sulfanyl}ethyl)pyridine (4)

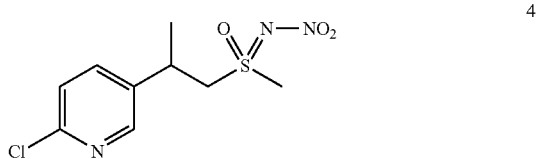

4

A) 2-(6-Chloropyridin-3-yl)propanenitrile

To a freshly made lithium diisopropamide (LDA) (0.1 mol) solution in THF-hexane (100 and 40 mL respectively) was added dropwise a solution of 3-cyanomethyl-6-chloropyridine (14.5 g, 0.095 mol) in THF (50 mL) at −78° C. The addition was at such a rate that the reaction temperature did not rise above −65° C. After the addition was complete, the mixture was stirred at this temperature for 30 min, and then slowly transferred via cannula to a cold stirred solution of iodomethane (28.38 g, 0.2 mol) in THF (100 mL) at −78° C. The rate of transfer was again at such a rate that the reaction temperature did not rise above −65° C. After the addition was over, the mixture was stirred at −78° C. for 30 min, then the temperature allowed to rise to −20° C. and the reaction was quenched with 2 N HCl (200 mL). Saturated sodium chloride solution (100 mL) was added and the phases separated. The aqueous phase was washed with ether (2×100 mL). The organic phases were combined, washed with brine and dried over $Na_2SO_4$. The solvent was evaporated to give a dark oil which was purified on silica gel using 15% acetone in hexane (v/v) to give 9.0 g of the desired cyano product in 57% yield:

m.p. 67-69° C. (after recrystallization from hexane-ether that resulted in pale yellow needles): IR: 2242 $cm^{-1}$.

B) 2-(6-Chloropyridin-3-yl)propanoic acid

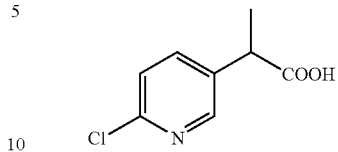

A stirred solution of 2-(6-chloropyridin-3-yl)propanenitrile (7.5 g, 50 mmol) and concentrated hydrochloric acid (70 mL) was heated at reflux for 3 hrs then cooled to room temperature. The solution was treated with charcoal and then filtered through celite. The pH of the filtrate was carefully adjusted to 4-5 by the addition of solid sodium carbonate. The resulting mixture was extracted with $CH_2Cl_2$ (3×75 mL). The organic phases were combined and dried over $MgSO_4$ and the solvent was evaporated to give 5.40 g of the desired acid in 65% yield as a yellow liquid which solidified upon standing: $^1H$ NMR ($CDCl_3$): δ 9.75 (bs, 1H, OH).

C) 2-Chloro-5-(1-methyl-2-{methyl(oxido)[oxido (oxo)hydrazono]-λ⁴-sulfanyl}ethyl)pyridine (4)

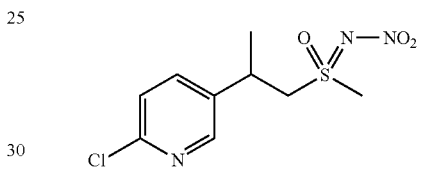

4

The compound (4) was prepared from 2-(6-chloropyridin-3-yl)propanoic acid by a six-step procedure as described in Example I: reduction of the acid to form alcohol, tosylation of the alcohol, substitution of the resulting tosylate to sulfide, oxidation of the sulfide to sulfoxide, imination of the sulfoxide to sulfoximine, and N-nitration of the sulfoximine with nitric acid and acetic anhydride. $[M+H]^+$: 278, 280; δ 3.16, 3.22 (2s, diastereomeric S—$CH_3$).

Example IV

Preparation of 2-[(6-chloropyridin-3-yl)methyl]-1-oxidohexahydro-1λ⁴-thiopyran-1-ylidenecyanamide (5)

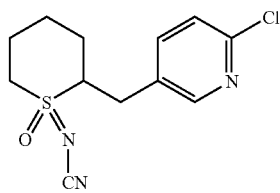

5

A) 1-Oxidohexahydro-1λ⁴-thiopyran-1-ylidenecyanamide (6)

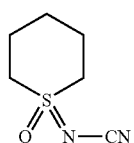

6

Thiane-1-oxide was made by oxidation of thiane with mCPBA. The procedure was as described above in Example I-F.

Thiane-1-imine-1-oxide was prepared by the following procedure: To a solution of freshly made O-mesitylsulfonylhydroxylamine (Johnson, C. R.; Robert A. Kirchhoff, R. A.; Corkins, H. G. *J. Org. Chem.* 1974, 39, 2458) (8.82 g, 41 mmol) in $CH_2Cl_2$ (80 mL) was added a solution of thiane-1-oxide (2.45 g, 20 mmol) in $CH_2Cl_2$ (70 mL) over a period of 1.5 h and the mixture was then stirred at room temperature overnight. Aqueous 10% NaOH solution (50 mL) was added to the mixture, which was stirred at room temperature for 10 min. The organic layer was separated and the aqueous phase was extracted with $CH_2Cl_2$ (50 mL). The combined organic layer was dried over $Na_2SO_4$, filtered, concentrated, and purified on silica gel to give 0.77 g of the desired sulfoximine The aqueous phase that retained most of the product was extracted continuously with chloroform for 3 h. The chloroform solution was then dried over $Na_2SO_4$, filtered and concentrated to give additional 1.84 g of analytically pure product as a yellowish oil. The combined yield from the two procedures was 2.61 g (94%). $[M+1]^+$: 134.

N-Cyano sulfoximine (6) was prepared from thiane-1-imine-1-oxide using cyanogen bromide by the method described above in Example I-I.

B) 2-[(6-Chloropyridin-3-yl)methyl]-1-oxidohexahydro-1$\lambda^4$-thiopyran-1-ylidenecyanamide (5)

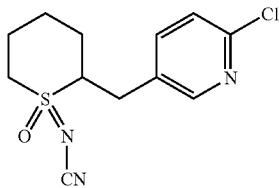

5

2-Chloro-5-iodomethylpyridine was first prepared by following procedure: A suspension of 2-chloro-5-chloromethylpyridine (16.2 g, 0.1 mol) and sodium idodide (22.3 g, 0.15 mol) in acetone (200 mL) was heated to reflux for 3 h and then the solvent acetone was removed by rotary evaporator. The remaining mixture was suspended in $CH_2Cl_2$ and the solid was filtered off. The filtrate was concentrated and the residue was loaded on a silica gel column and eluted with 1:4 EtOAc-hexane to give 20.8 g of 2-chloro-5-iodomethylpyridine as brown oil in 82% yield, which turned into solid once being dried under vacuum.

To a solution of N-cyano sulfoximine (6) (0.158 g, 1.0 mmol) in THF (8 mL) was added 2.5 M n-BuLi in hexane (0.44 mL, 1.1 mmol) at –78° C. After 1 h, a suspension of 2-chloro-5-iodomethylpyridine (0.28 g, 1.1 mmol) in THF (3 mL) was added in one portion via a syringe. After 30 min, the mixture was stirred at room temperature for 3 h. The reaction was quenched with saturated aqueous $NH_4Cl$ solution, extracted with $CH_2Cl_2$ three times, washed with brine, dried over $Na_2SO_4$, filtered, and concentrated. The residue was purified on preparative reverse phase HPLC using 55% MeCN in water as solvent to give 0.049 g of the desired product in 17% yield: $[M+H]^+$=284, 286.

Example V

Preparation of methyl 2-[(6-chloropyridin-3-yl)methyl]-1-oxidotetrahydro-1H-1$\lambda^4$-thien-1-ylidenecarbamate (7)

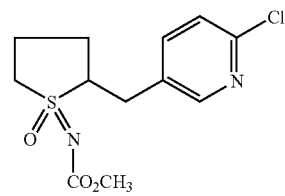

7

A) 2-Chloro-5-[(1-oxidotetrahydrothien-2-yl)methyl]pyridine

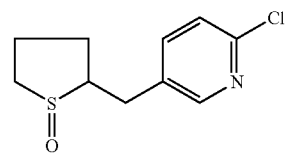

Tetramethylene sulfoxide (6.5 g, 62 mmol) was dissolved in 30 mL anhydrous THF, stirred and cooled to –70° C. and then treated with 2.5 M n-BuLi in hexane (24 mL, 61 mmol) over a period of 10 min. The temperature was raised to –20 to –30° C. (Liquid $N_2$/o-xylene bath) and the mixture was stirred for a further 30 min. The mixture was cooled to –70° C. and treated dropwise with a solution of 6-chloro-3-chloromethylpyridine in 15 mL THF. The reaction was stirred for 2 h at –70° C. and then treated dropwise with trifluoroacetic acid (8.0 g, 70 mmol). The mixture was warmed to room temperature, poured into 75 mL water and extracted with dichloromethane (2×50 mL). The combined organic extracts were washed with dilute sodium bicarbonate and saturated NaCl, dried over $Na_2SO_4$ and concentrated. The residue was chromatographed on silica gel with 5% methanol in dichloromethane to give 2.5 g of the desired sulfoxide as a brown oil in 35% yield.

B) 2-[(6-Chloropyridin-3-yl)methyl]tetrahydro-1H-1$\lambda^4$-thiophen-1-imine 1-oxide

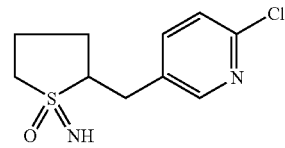

2-[(6-Chloropyridin-3-yl)methyl]tetrahydro-1H-1$\lambda^4$-thiophen-1-imine-1-oxide was prepared from 2-chloro-5-[(1-oxidotetrahydrothien-2-yl)methyl]-pyridine by the method as described in Example I-H using $NaN_3$ as the iminating agent.

Separation of the two diastereomers of the sulfoximine: A crude diastereomer mixture (~3:1 ratio of diastereomers) of the above sulfoximine (20, 0.8 g) was added to a 4 mm silica gel plate of a Chromatron® chromatographic unit. The material was eluted with a solvent gradient of hexane/acetone starting with a 50:50 mixture, then increasing the acetone concentration in 5% increments every 200 mL. Also after every 200 mL of solvent was added, then plate was partially dried before the next increment of solvent was added. In this manner good separation was achieved with only a minor amount of mixed materials eluting between the two purified diastereomers. Eluting first was the minor diastereomer which solidified upon standing. $^{13}$C NMR (CDCl$_3$): 20.4, 30.0, 30.6, 54.5, 64.0, 124.2, 131.9, 139.0, 149.7, and 150.0. Eluting second was the major diastereomer (yellow gum). $^{13}$C NMR (CDCl$_3$): 21.0, 30.1, 30.7, 55.9, 64.7, 124.1, 131.9, 139.3, 149.9, 150.0. Both diastereomers showed a [M+H]$^+$ at 245 and 247.

The diastereomerically pure N-substituted sulfoximine was made from the correspondent diastereomeric pure sulfoximine.

C) Methyl 2-[(6-chloropyridin-3-yl)methyl]-1-oxidotetrahydro-1H-1λ$^4$-thien-1-ylidenecarbamate (7)

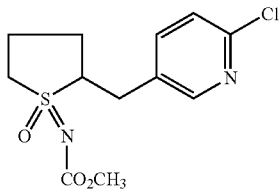

To a stirred solution of 2-[(6-chloropyridin-3-yl)methyl]tetrahydro-1H-1λ$^4$-thiophen-1-imine-1-oxide (diastereomeric mixture, 0.20 g, 0.82 mmol) and DMAP (0.104 g, 0.85 mmol) in CH$_2$Cl$_2$ (5 mL) was added methyl chloroformate (0.077 g, 0.82 mmol) in one portion and the resulting solution was stirred for 30 min at room temperature. The reaction mixture was diluted with CH$_2$Cl$_2$ (20 mL), washed with 1 N HCl (20 mL) and dried over MgSO$_4$ and the solvent evaporated to give 0.23 g of the analytically pure desired product (7) as a yellow gum in 93% yield. [M+H]$^+$=303, 305.

Example VI

Preparation of [1-(6-chloropyridin-3-yl)ethyl](methyl)oxido-λ$^4$-sulfanylidenecyanamide (8) and [1-(6-chloropyridin-3-yl)-1-methylethyl](methyl)oxido-λ$^4$-sulfanylidenecyanamide (9)

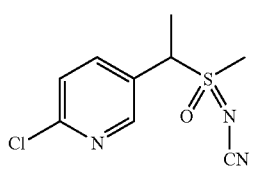

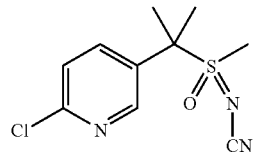

A) [(6-Chloropyridin-3-yl)methyl](methyl)oxido-λ$^4$-sulfanylidene-cyanamide (10)

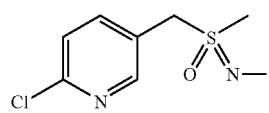

[(6-Chloropyridin-3-yl)methyl](methyl)oxido-λ$^4$-sulfanylidene-cyanamide (10) was prepared from the corresponding sulfoximine 2-chloro-5-[methylsulfonimidoyl)methyl]pyridine by the method described in Example I-I using cyanogen bromide as the N-cyanating agent.

2-Chloro-5-[(methylsulfonimidoyl)methyl]pyridine was prepared form the corresponding sulfide via a two-step process as described in Example I-G and I-H: oxidation of the sulfide to sulfoxide followed by imination of the sulfoxide.

B) [1-(6-Chloropyridin-3-yl)ethyl](methyl)oxido-λ$^4$-sulfanylidenecyanamide (8) and [1-(6-chloropyridin-3-yl)-1-methylethyl](methyl)oxido-λ$^4$-sulfanylidenecyanamide (9)

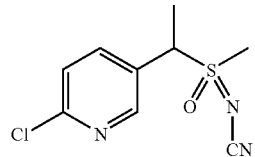

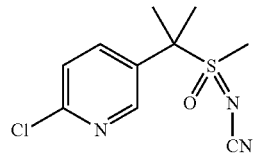

To a solution of N-cyano sulfoximine (10) (0.34 g, 1.5 mmol) and hexamethyl phosphoramide (HMPA) (0.14 mL, 0.8 mmol) in 15 mL anhydrous THF was added dropwise a solution of 0.5 M KHMDS in toluene (3.6 mL, 1.8 mmol) at −78° C. After 45 min, iodomethane (0.11 mL, 1.8 mmol) was added in one portion via a syringe. Ten minutes later, the temperature was allowed to rise to 0° C. After stirring for 1.5 h., the reaction was quenched with saturated aqueous NH$_4$Cl, diluted with brine and extracted with CH$_2$Cl$_2$ three times. The combined organic layer was dried over Na$_2$SO$_4$, filtered and concentrated. The residue was first purified on silica gel twice, first time eluted with 2% MeOH in CH$_2$Cl$_2$ (v/v) and the second time with 9% acetone in CH$_2$Cl$_2$ (v/v) to give 0.217 g of mono methylated N-cyano sulfoximine (8) in 60% yield ([M−H]$^+$=242, 244) as a mixture of disastereomers and 0.066 g of dimethylated N-cyano sulfoximine (9) in 17% yield ([M−H]$^+$=256, 258).

The ratio of the amount of the two compounds varied with the amount of the base added. In addition, the dimethylated compound (9) can also be made from the mono-methylated molecule (8) by the same method.

Example VII

Preparation of 2-[(2-chloro-1,3-thiazol-5-yl)methyl]-1-oxidotetrahydro-1H-1λ⁴-thien-1-ylidenecyanamide (11)

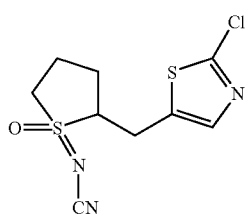

A) 1-Oxidotetrahydro-1H-1λ⁴-thien-1-ylidenecyana-mide (12)

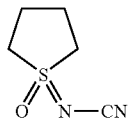

1-Oxidotetrahydro-1H-1λ⁴-thien-1-ylidenecyanamide (12) was prepared from tetrahydrothiophene-1-oxide by a two-step procedure as described in Example I-H and I-I: imination of the sulfoxides with sodium azide and N-cyanation of the resulting sulfoximine with cyanogen bromide. $^{13}$C NMR (CDCl$_3$): 112.3, 52.9.

B) 2-[(2-Chloro-1,3-thiazol-5-yl)methyl]-1-oxidotetrahydro-1H-1λ⁴-thien-1-ylidenecyanamide

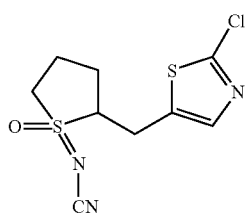

2-Chloro-5-(iodomethyl)thiazole was first prepared from 2-chloro-5-chloromethylthiazole using sodium iodide as iodinating agent in acetone by the method as described in Example IV-B.

1-Oxidotetrahydro-1H-1λ⁴-thien-1-ylidenecyanamide (12) (2.0 g, 14 mmol) was dissolved in 30 mL anhydrous THF, cooled to −78° C. and treated with 2.5 M n-butyl lithium in hexane (5.5 mL, 14 mmol). After 2 h at −78° C., the anion was treated dropwise with a solution of 2-chloro-5-(iodomethyl)thiazole in 10 mL anhydrous THF. After stirring for 4 h at −78° C., the mixture was allowed to warm to 25° C. and stir for 19 h. HPLC showed a 90% conversion of the iodide into a mixture of the mono and dialkylated sulfoximines. The reaction was quenched with sat. NH$_4$Cl solution and worked up in ethyl acetate/water. After evaporation of the organic phase, the residue was chromatographed by preparative HPLC on a 50 mm×250 mm YMC AQ column with 60% acetonitrile/40% 0.1% H$_3$PO$_4$ to give the desired mono alkylated product 0.32 g (7.3%) as a pale yellow oil ([M+H]$^+$=276, 278).

Example VIII

Preparation of (6-Ethoxypyridin-3-yl)(methyl)oxido-λ⁴-sulfanylidenecyanamide (42)

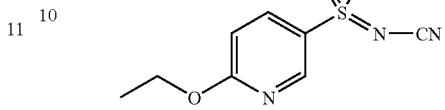

A) 2-Chloro-5-methylsulfinylpyridine

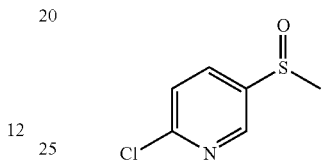

To a solution of 2-chloro-5-bromopyridine in 110 mL anhydrous ether under nitrogen was added n-BuLi at −78° C. over a period of 5 min. The mixture was then stirred at this temperature for 1 h and methyl disulfide was added in one portion via a syringe. After 30 min, the temperature was allowed to warm to room temperature and the reaction was continued for 1 h. The reaction was quenched with saturated NH$_4$Cl at −78° C. and half-saturated brine solution was added to the mixture. After separation of the two phases, the aqueous phase was extracted with ether two more times. The combined organic layer was washed with brine, dried over Na$_2$SO$_4$, filtered, concentrated and purified on silica gel using 20% ethyl ether in hexane as eluent to give 3.7 g of 2-chloro-5-methyl-thiopyridine as a pale brownish oil in 78% yield.

2-Chloro-5-methylsulfinylpyridine was prepared by the method described in Example I-F from 2-chloro-5-methylthiopyridine using mCPBA as oxidant.

B) 2-Ethoxy-5-(methylsulfonimidoyl)pyridine

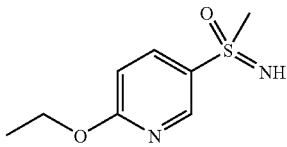

Following the procedure as described in Example I-G using NaN$_3$ and concentrated sulfuric acid as iminating agent in chloroform solvent containing ethanol stabilizer, both sulfoximines 2-chloro-5-(methylsulfonimidoyl)pyridine (m/e: [M]$^+$=190, 192) and 2-ethoxy-5-(methylsulfonimidoyl)pyridine (m/e: [M]$^{30}$=200) were formed. If more than one equivalent of ethanol was added into the reaction mixture, 2-ethoxy-5-(methylsulfonimidoyl)pyridine was almost formed exclusively. 2-Ethoxy-5-(methylsulfonimidoyl)pyridine can also be prepared from 2-chloro-5-(methylsulfonimidoyl)pyridine by heating it in ethanol in the presence of acid such as hydrogen chloride.

C) (6-Ethoxypyridin-3-yl) (methyl)oxido-λ⁴-sulfanylidenecyanamide

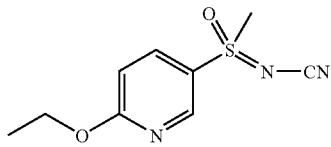

42

N-cyano 2-ethoxy sulfoximine (42) (m/e: [M]⁺=225) was prepared from 2-ethoxy-5-(methylsulfonimidoyl)pyridine using cyanogen bromide as N-cyanating agent by the method described in Example I-I.

Example IX

Preparation of (2-Chlorothiazole-4-yl)methyl(methyl)oxido-λ⁴-sulfanylidenecyanamide (43)

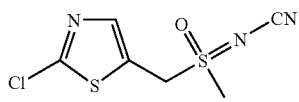

43

A) (2-Chlorothiazole-4-yl)methyl(methyl)oxido-λ⁴-sulfinylidenecyanamide

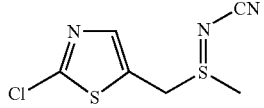

To a stirred solution of the 2-chloro-4-methylthiomethylthiazole (1.79 g, 10 mmol) and cyanamide (0.84 g, 20 mmol) in CH₂Cl₂ (30 mL) cooled to 0° C. was added iodobenzene diacetate in one portion and the resulting mixture was stirred at 0° C. for 1 h. The reaction was quenched with sodium bisulfite solution. The organic phase was separated and the aqueous phase extracted with CH₂Cl₂ one more time. The combined organic layer was dried over Na₂SO₄, filtered, concentrated, and purified on silica gel using 60% acetone in hexane to give 1.62 g of the product as a white crystalline solid in 74% yield. m.p. 106-108° C.

B) (2-Chlorothiazole-4-yl)methyl(methyl)oxido-λ⁴-sulfanylidenecyanamide (43)

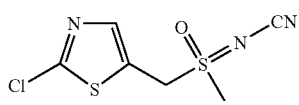

43

To a stirred solution of the 80% 3-chloroperoxybenzoic acid (2.1 g, 9.8 mmol) in ethanol (25 mL) cooled to 0° C. was added a solution of potassium carbonate (2.7 g, 19.6 mmol) in water (15 mL). The resulting mixture was stirred at 0° C. for 20 min. Then a solution of the sulfilimine starting material (1.43, 6.5 mmol) in ethanol (20 mL) was added at once. The resulting mixture was stirred for 40 min at 0° C. and saturated sodium bisulfite was added to quench the excess peracid. Most of the solvent was evaporated and water was added to the residue. The insoluble solid was filtered, washed with several portions of water, and then dried under vacuum to give 1.02 g of the desired sulfoximine product as a white crystalline solid in 65% yield, m.p. 113-114° C.

Example X

Preparation of (1-oxido-2-phenyltetrahydro-1H-11⁴-thien-1-ylidene)cyanamide (22)

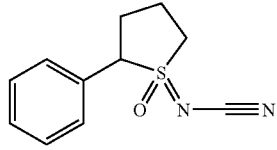

22

A) (2-phenyltetrahydro-1H-11⁴-thien-1-ylidene)cyanamide

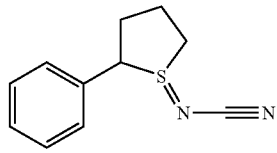

To a stirred mixture of 2-phenyltetrahydrothiophene (prepared from tetrahydrothiophene by the method described in Scheme G) (0.82 g, 0.005 mol) and cyanamide (0.42 g, 0.01 mol) in CH₂Cl₂ (20 mL) cooled to 0° C. was added iodobenzene diacetate (3.22 g, 0.01 mol) in one portion. The resulting solution was stirred at 0° C. for 30 min followed by room temperature for 30 min. Water (30 mL) was added to the red reaction mixture and the organic phase separated. The aqueous phase was extracted with CH₂Cl₂ and the combined organic phases were dried (MgSO₄) and the solvent evaporated. The red reside was chromatographed on a silica gel column and eluted with 1:1 hexanes-acetone to give 0.57 g (56%) of the desired compound as an orange gum.

B) (1-oxido-2-phenyltetrahydro-1H-11⁴-thien-1-ylidene)cyanamide (22)

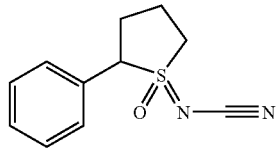

22

To a solution of 3-chloroperoxybenzoic acid (0.41 g, 0.0024 mol) in 95% EtOH (4 mL) cooled to 0° C. was added a solution of K₂CO₃ (0.66 g, 0.0048 mol) in water (3 mL). The resulting mixture was stirred for 20 min at 0° C. then a solution of (2-phenyltetrahydro-1H-11$^4$-thien-1-ylidene)cyanamide (0.25 g, 0.0012 mol) in 95% EtOH (10 mL) was added in one portion. The ice bath was removed and stirring was continued for 1 hr. Most of the solvent was removed in vacuo and water (10 mL) was added. The remaining 3-chloroperoxybenzoic acid was quenched by addition of sodium bisulfite and the pH adjusted to ~12 by the addition of 50% NaOH. The resulting mixture was extracted with CH₂Cl₂ (2×30 mL). The organic fractions were combined, dried (MgSO₄) and the solvent evaporated to give the title compound as a clear oil (0.21 g, 80%) which did not require further purification. $^1$H NMR analysis was consistent with the compound being a 56:44 mixture of diastereomers.

Table 1 summarizes those compounds prepared in Examples I-X as well as lists other compounds of the invention prepared according to the procedures described above.

TABLE 1

| Comp # | Structure | Characterization |
|---|---|---|
| 2 | 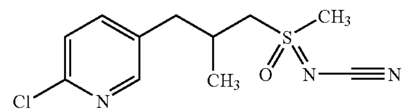 | [M + H]⁺: 272, 274; IR: 2189 cm⁻¹ |
| 3 | 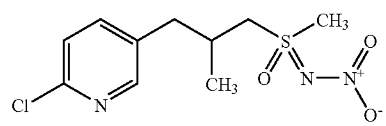 | [M + H]⁺: 292, 294 |
| 4 | 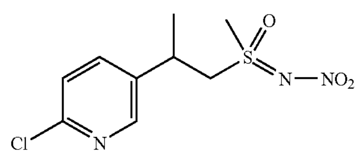 | [M + H]⁺: 278, 280 |
| 5 | 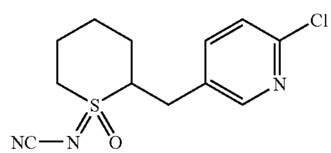 | [M + H]⁺: 284, 286 |
| 6 | 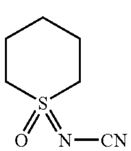 | [M − H]⁺: 159 |
| 7 | 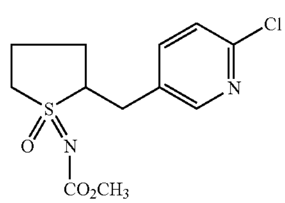 | [M + H]⁺: 303, 305 |
| 8 | 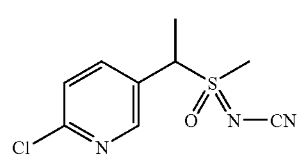 | [M − H]⁺: 242, 244 |
| 9 | 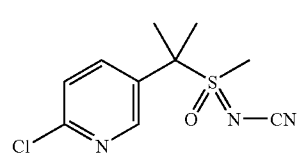 | [M − H]⁺: 256, 258 |

TABLE 1-continued

| Comp # | Structure | Characterization |
|---|---|---|
| 10 | 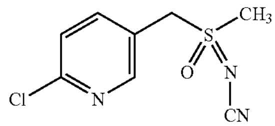 | [M − H]+: 228 |
| 11 | 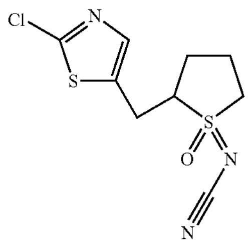 | [M + H]+: 276, 278 |
| 12 | 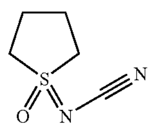 | $^{13}$C NMR (CDCl$_3$): δ 112.3, 52.9 |
| 13 | 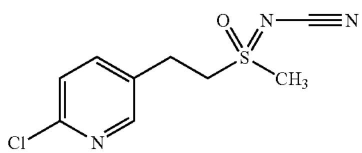 | [M + H]+: 244, 246; IR: 2180 cm$^{-1}$ |
| 14 | 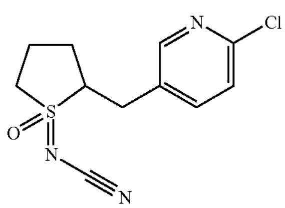 | [M − H]+: 268, 270 |
| 15 | 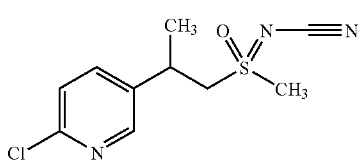 | [M + H]+: 258, 260; IR: 2188 cm$^{-1}$ |
| 16 | 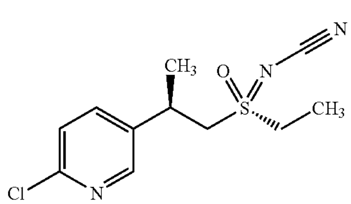 | Chiral [M + H]+: 272, 274; IR: 2189 cm$^{-1}$ |
| 17 | 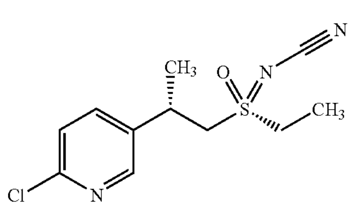 | Chiral [M + H]+: 272, 274; IR: 2192 cm$^{-1}$ |

TABLE 1-continued

| Comp # | Structure | Characterization |
|---|---|---|
| 18 | 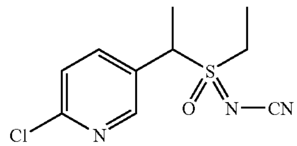 | [M + H]⁺: 258, 260; δ 7.90 (dd, 1 H) |
| 19 | 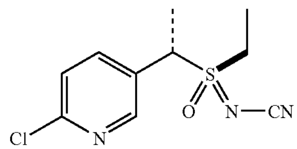 | [M + H]⁺: 258, 260; δ 7.86 (dd, 1 H) |
| 20 | Chiral | [M + H]⁺: 270, 272; ¹³C NMR: δ 20.14 |
| 21 | 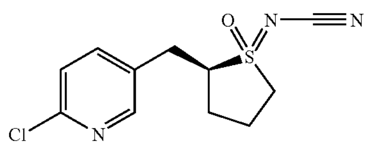 | [M + H]⁺: 270, 272; ¹³C NMR: δ 21.16 |
| 22 | 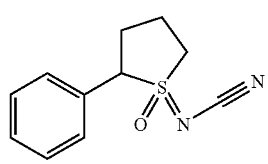 | [M + H]⁺: 221; IR: 2192 cm⁻¹ |
| 23 | 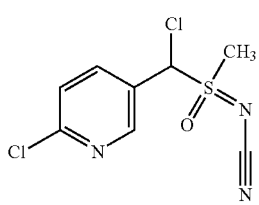 | ¹H NMR (CDCl₃): δ 7.05, 6.92 (2 s, 1 H, diastereomers) |
| 24 | 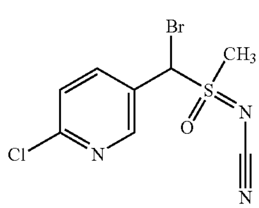 | ¹H NMR (CDCl₃): δ 6.42, 6.34 (2 s, 1 H, diastereomers) |
| 25 | 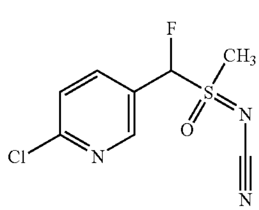 | [M + H]⁺: 248, 250 |

TABLE 1-continued

| Comp # | Structure | Characterization |
|---|---|---|
| 26 | 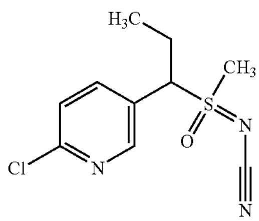 | [M − H]+: 256, 258 |
| 27 | 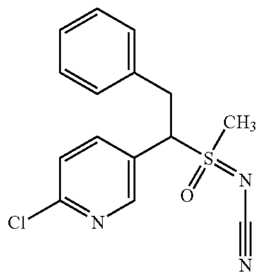 | [M − H]+: 318, 320 |
| 28 | Chiral | [M − H]+: 242, 244; 1H NMR (DMSO): δ 3.419 (s, 3 H) |
| 29 | Chiral | [M − H]+: 242, 244; 1H NMR (DMSO): δ 3.406 (s, 3 H) |
| 30 | 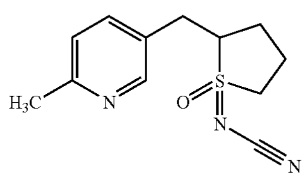 | [M − H]+: 248 |
| 31 | 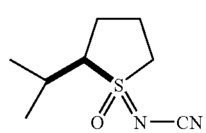 | [M + H]+: 187; IR: 2192 cm−1 |
| 32 | 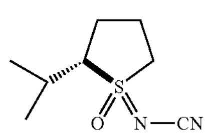 | [M + H]+: 187; IR: 2188 cm−1 |
| 33 | 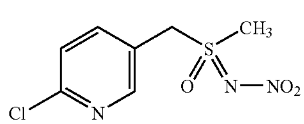 | [M − H]+: 250, 252 |
| 34 | 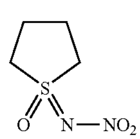 | 13C NMR (CDCl3): δ 52.3, 24.0 |

TABLE 1-continued

| Comp # | Structure | Characterization |
|---|---|---|
| 35 | 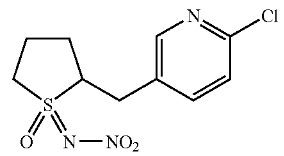 | $^{13}$C NMR (CDCl$_3$): δ 66.29, 63.85 |
| 36 | 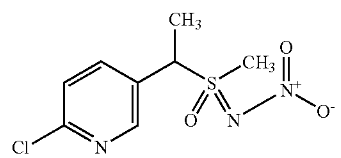 | [M + H]$^+$: 264, 266 |
| 37 | 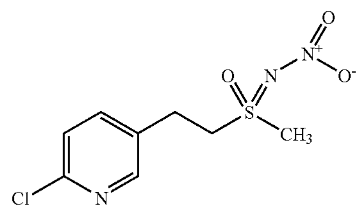 | [M + H]$^+$: 264, 266 |
| 38 | 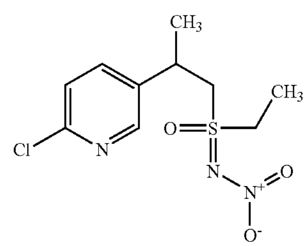 | [M + H]$^+$: 292, 294 |
| 39 | 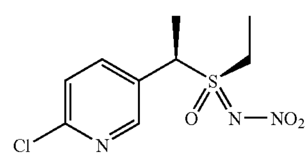 | [M + H]$^+$: 278, 280; $^1$H NMR: δ 4.92 (q, 1 H) |
| 40 | 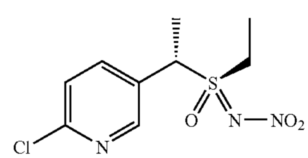 | [M + H]$^+$: 278, 280; $^1$H NMR: δ 5.10 (q, 1 H) |
| 41 | Chiral | [M + H]$^+$: 290, 292: $^{13}$C NMR: δ 66.41 |
| 42 | 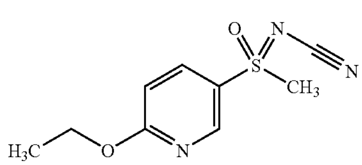 | [M]$^+$: 225 |

TABLE 1-continued

| Comp # | Structure | Characterization |
|---|---|---|
| 43 | (2-chloro-thiazol-5-yl)methyl-S-methyl-N-cyano sulfoximine structure | [M + H]⁺: 236 |

Example IX
Insecticidal Testing

The compounds identified in Table 2 were prepared using the procedures illustrated in the foregoing examples, and the compounds were tested against cotton aphid, green peach aphid, corn earworm, beet armyworm, fruit fly, mosquito, sweet potato whitefly and Colorado potato beetle using procedures described hereinafter.

TABLE 2

| Comp # | CA 200 | CA 50 | CEW 50 | BAW 50 | BAW SYM | FF SYM | FF 25 | YFM 26 | SPW 200 | CPB 50 |
|---|---|---|---|---|---|---|---|---|---|---|
| 2 | A | B | G | G | G | G | G | G | H | H |
| 3 | B | G | G | G | G | G | G | G | H | H |
| 4 | F | G | G | G | F | G | G | G | H | H |
| 5 | A | A | G | G | E | G | G | E | H | H |
| 6 | G | G | G | G | G | G | G | G | H | H |
| 7 | B | G | G | G | G | G | G | G | H | H |
| 8 | A | A | G | G | E | A | A | A | A | A |
| 9 | A | A | G | G | F | A | C | A | H | H |
| 10 | A | A | G | G | F | A | A | A | A | B |
| 11 | A | A | G | G | D | G | D | A | H | H |
| 12 | A | A | D | F | A | A | D | G | B | H |
| 13 | A | A | G | G | F | G | G | G | A | H |
| 14 | A | A | G | G | G | G | F | A | H | H |
| 15 | A | B | G | G | G | G | G | G | H | H |
| 16 | A | A | G | G | F | G | G | G | H | H |
| 17 | A | A | G | G | G | G | G | G | H | H |
| 18 | A | A | G | F | F | G | G | G | B | H |
| 19 | A | A | G | G | G | G | F | G | C | H |
| 20 | A | A | G | G | B | F | F | A | A | A |
| 21 | A | A | G | G | G | G | G | B | H | H |
| 22 | A | B | G | G | F | G | G | G | H | H |
| 23 | A | A | G | G | F | A | A | A | H | H |
| 24 | A | A | G | G | F | F | A | A | H | H |
| 25 | A | A | G | G | G | B | C | A | H | H |
| 26 | A | A | G | G | F | A | A | A | H | H |
| 27 | A | A | G | G | G | G | G | B | H | H |
| 28 | A | A | G | G | D | A | A | A | A | H |
| 29 | A | A | G | G | A | A | A | A | A | H |
| 30 | A | A | G | G | G | G | G | G | H | H |
| 31 | A | G | G | G | G | G | G | G | H | H |
| 32 | B | G | G | G | E | G | G | G | H | H |
| 33 | A | A | G | G | F | F | G | G | G | H |
| 34 | A | A | G | G | F | G | F | G | G | H |
| 35 | A | A | G | G | F | D | F | B | A | B |
| 36 | A | A | G | G | G | F | F | G | G | H |
| 37 | A | A | G | G | G | G | G | G | H | H |
| 38 | A | B | G | G | G | G | G | F | H | H |
| 39 | A | G | G | G | G | G | F | G | H | H |
| 40 | B | G | G | G | G | G | G | G | H | H |
| 41 | A | A | G | G | G | G | F | A | A | A |
| 42 | A | C | G | G | G | G | G | G | H | H |
| 43 | B | C | G | G | G | F | F | G | H | H |

CA 200 refers to % control at 200 ppm against cotton aphid in foliar spray tests,
CA 50 refers to % control at 50 ppm against cotton aphid in foliar spray tests,
CEW 50 refers to % mortality at 50 μg/cm2 against corn earworm in dietary tests,
BAW 50 refers to % mortality at 50 μg/cm2 against beet armyworm in dietary tests,
BAW SYM refers to % showing intoxicated symptoms at 10 μg/larva against beet armyworm in injection tests,
FF SYM refers to % showing intoxicated symptoms at 25 μg/cm2 against fruit fly in dietary tests,
FF 25 refers to % mortality at 25 μg/cm2 against fruit fly in dietary tests,
YFM 26 refers to % control at 26 ppm against yellow fever mosquito in submerge tests,
SPW 200 refers to % control at 200 ppm against sweet potato whitefly in foliar spray tests,
CPB 50 refers to % control at 50 ppm against Colorado potato beetle in foliar spray tests.

In each case of Table 2 the rating scale is as follows:

| % Control (or Mortality) | Rating |
|---|---|
| 90-100 | A |
| 80-89 | B |
| 70-79 | C |
| 60-69 | D |
| 50-59 | E |
| Less than 50 | F |
| Inactive | G |
| Not tested | H |

The compounds that showed high activities against cotton aphid in Table 2 were further tested with multiple lower doses (rundown assays) against cotton aphid using procedures described hereinafter. Results are shown in Table 3.

TABLE 3

| | % Control at ppm, against cotton aphid | | | | | | |
|---|---|---|---|---|---|---|---|
| Comp # | 0.012 | 0.049 | 0.195 | 0.78 | 3.12 | 12.5 | 50 |
| 20 | H | B | A | A | A | A | A |
| 41 | H | C | A | A | A | A | A |
| 12 | H | H | G | E | E | A | A |
| 34 | H | C | B | B | A | A | A |
| 36 | H | F | F | C | A | A | A |
| 13 | H | G | F | A | A | A | A |
| 28 | A | A | A | A | A | H | H |
| 29 | A | A | A | A | A | H | H |

In each case of Table 3 the rating scale is the same as that used for Table 2.

The compounds that showed high activities against cotton aphid in Table 2 were further tested in rundown assays against green peach aphid using procedures described hereinafter. Results are shown in Table 4.

TABLE 4

| | % Control at ppm, against green peach aphid | | | | | | |
|---|---|---|---|---|---|---|---|
| Comp # | 0.012 | 0.049 | 0.195 | 0.78 | 3.12 | 12.5 | 50 |
| 20 | H | F | F | F | F | A | A |
| 41 | H | F | F | E | D | A | A |
| 12 | H | H | G | G | G | F | F |
| 34 | H | F | F | E | D | D | D |
| 36 | H | F | E | D | C | A | A |
| 13 | H | G | G | F | C | C | B |
| 28 | F | F | B | A | A | H | H |
| 29 | F | D | A | A | A | H | H |

In each case of Table 4 the rating scale is the same as that used for Table 2.

The compounds that showed high activities against sweet potato whitefly in Table 2 were further tested in rundown assays against sweet potato whitefly using procedures described hereinafter. Results are shown in Table 5.

TABLE 5

| | % Control at ppm, against sweet potato whitefly | | | |
|---|---|---|---|---|
| Comp # | 0.4-0.78 | 2-3.13 | 10-12.5 | 50 |
| 10 | F | D | A | A |
| 20 | F | F | A | A |

TABLE 5-continued

| | % Control at ppm, against sweet potato whitefly | | | |
|---|---|---|---|---|
| Comp # | 0.4-0.78 | 2-3.13 | 10-12.5 | 50 |
| 8 | A | A | A | A |
| 28 | A | A | A | A |
| 29 | A | A | A | A |

In each case of Table 5 the rating scale is the same as that used for Table 2.

The compounds that showed high activities against Colorado potato beetle in Table 2 were further tested in rundown assays against Colorado potato beetle using procedures described hereinafter. Results are shown in Table 6.

TABLE 6

| | % Control at ppm, against Colorado potato beetle | | | |
|---|---|---|---|---|
| Comp # | 0.78 | 3.13 | 12.5 | 50 |
| 20 | F | F | A | A |
| 41 | F | F | D | A |
| 10 | H | G | E | B |
| 8 | H | D | A | A |

In each case of Table 6 the rating scale is the same as that used for Table 2.

Insecticidal Test for Cotton Aphid (*Aphis gossypii*).

Squash with fully expanded cotyledon leaves were trimmed to one cotyledon per plant and infested with cotton aphid (wingless adult and nymph) 1 day prior to chemical application. Each plant is examined before chemical application to ensure proper infestation (ca. 30-70 aphids per plant). Compounds (3 mg) were dissolved in 3 mL of acetone:methanol (50:50) solvent, forming stock solutions of 1000 ppm. The stock solutions were then diluted with 0.025% Tween 20 (in $H_2O$) to make 200 and 50 ppm spray solutions. A handheld Devilbiss sprayer was used to apply the spray solutions until runoff to both sides of the squash cotyledon leaves. Four plants (4 replications) were used for each concentration of each compound. Reference plants (solvent check) were sprayed with 0.025% Tween 20 only. Treated plants were held in a holding room for 3 days at approximately 23° C. and 40% RH before the number of live aphids on each plant was recorded. Insecticidal activity was measured by Corrected % Control using Abbott's correction formula and presented in Table 2:

Corrected % Control=100*(X−Y)/X where

X=No. of live aphids on solvent check plants

Y=No. of live aphids on treated plants

Compounds that showed high activity (high Corrected % Control) from the above basic screening were further assayed in rundown assays using the same procedures with 0.012, 0.049, 0.195, 0.78, 3.13, 12.5 and/or 50 ppm as test doses. The Corrected % Control values from these rundown assays are given in Table 3.

Insecticidal Test for Green Peach Aphid (*Myzus persicae*).

Cabbage seedlings grown in 3-inch pots, with 2-3 small (3-5 cm) true leaves, were used as test substrate. The seedlings were infested with 20-50 green peach aphids (wingless adult and nymph) 2-3 days prior to chemical application. Four seedlings were used for each treatment. Five milligrams of test compounds were dissolved in 5 mL of acetone:methanol (50:50) solvent. The solutions were then diluted with 0.025% Tween 20 (in $H_2O$) to make 0.012, 0.049, 0.195, 0.78, 3.13, 12.5 and/or 50 ppm spray solutions. A hand-held Devilbiss sprayer was used for spraying a solution to both sides of cabbage leaves until runoff. Reference plants (solvent check) were sprayed with 0.025% Tween 20 only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where

X=No. of live aphids on solvent check plants

Y=No. of live aphids on treated plants

The Corrected % Control values from these rundown assays are given in Table 4.

Insecticidal Test for Corn Earworm (*Helicoverpa zea*) and Beet Armyworm (*Spodoptera exigua*) in Dietary Assays.

Dietary assays were conducted in 128-well plastic trays. To prepare test solution, the test compound was formulated at 2000 ppm in 2 mL of acetone:water (9:1). A volume of 50 µl of the test solutions was pipetted upon the surface of 1 mL of lepidopteran diet (Southland Multi-Species Lepidopteran Diet) in each well of 128-well plastic trays. Eight wells (8 replications) were used for each treatment on each insect species. This application rate was equivalent to 50 µg/cm$^2$. A second-instar corn earworm or beet armyworm larva was placed upon the treated diet in each well once the solvent had been air-dried. Trays containing the treated diet and larvae were covered with self-adhesive transparent sheets and held in a growth chamber at 25° C., 50-55% RH, and 16 h light:8 h dark Observation were conducted 5 days after treatment and infestation. The number of dead insects is converted to % mortality that is given in Table 2.

% Mortality=100*X/Y where

X=No. of dead insects

Y=Total No. of insects tested (=8)

Insecticidal Test for Beet Armyworm (*Spodoptera exigua*) in Injection Assays.

Test solutions were prepared by dissolving 2 mg of tech grade compound in 100 µl of dimethyl sulfoxide or acetone. Each 4$^{th}$ instar beet armyworm larva was injected with 0.5 µl (10 µg of test compound per larva) solution using a Hamilton 10 µl 33½ gauge syringe. The test solution was injected into the abdomen of a larva, just underneath the cuticle and with the long axis of the syringe needle parallel to the long axis of the insect's body. A solvent blank and an untreated plate were included to each test to ensure validity. Six larvae were used for each treatment. Injected larvae were individually placed in the wells of 6-well polystyrene plates with a small amount of lepidopteran diet (Southland Multi-Species Lepidopteran Diet). Plates were held at room temperature in the lab and were graded at 1, 24, and 48 h. Intoxicated symptoms were observed at each time point. The number of larvae showing symptoms was converted to % Show Symptoms.

% Show Symptoms=100*X/Y where

X=No. of larvae showing symptoms

Y=Total No. of larvae tested (=6)

The results (% Show Symptom) from the 1 h observation are presented in Table 2.

Insecticidal Test for Fruit Fly (*Drosophila melanogaster*).

Polystyrene plates with 24 wells were filled with approximately 300 µl of an agar solution containing 20 g of agar in 1000 mL of 10% sucrose solution. Green or yellow food coloring was added to the agar solution as the color will be visible in the abdomen of the fly when ingested (providing an indication of ingestion observation). Prior to treatment, 1.5-cm filter paper disks were individually placed on the top of the solidified agar layer in the wells. Test solutions were prepared by adding 500 µl of acetone:water (2:1) solvent to 2 mg of tech grade compounds, then adding an additional 500 µl of 10% sucrose solution to provide final concentration of 2000 ppm. For the solvent blank, 500 µl of acetone:water (2:1) solvent was added to 500 µl of 10% sucrose solution. A volume of 25 µl of the formulated 2000 ppm solution was pipetted onto the filter paper in each well (equivalent to 25 µg/cm$^2$). Four wells (4 replications) were used for each compound. Plates were then placed in a fume hood for 30-45 minutes to allow solvent to evaporate. Test flies were placed in a refrigerator for 10-15 minutes and transferred onto a glass dish that was kept on ice. Chilled flies were transferred to the treated plates with a camel's hair brush. On average, 5-8 flies were used for each well. The plates were covered with lids immediately after the infestation and held at room temperature in the laboratory. Observation for intoxicated symptoms was conducted at 4 h and % mortality was recorded at 48 h. The number of flies showing symptoms was converted to % Show Symptoms and the number of dead flies was converted to % Mortality.

% Show Symptoms=100*X/Y where

X=No. of flies showing symptoms

Y=Total No. of flies tested

% Mortality=100*X/Y where

X=No. of dead flies

Y=Total No. of flies tested

Results are presented in Table 2.

Insecticidal Test for Mosquito (*Aedes aegypti*).

This test was designed to evaluate the insecticidal activity of compounds against yellow fever mosquito larvae through contact and ingestion. Micro-titer plates with 96 wells were treated with formulated compounds in dimethyl sulfoxide at 4000 ppm concentration. A Tomtec robotic system was used to dispense 1.5 µl of each formulated experimental solution into each well of the plates. Each compound was applied to 6 wells (6 replications). Subsequent to application, mosquito larvae (3 hours old following hatch) were suspended in water containing 0.4% mosquito diet (brewers yeast:liver powder=1:3) and transferred to the wells. A Labsystems Multidrop robotic system was used to dispense aliquots of 230 µl of this aqueous solution with 5-8 mosquito larvae into each well of the treated plates. The final test concentration was approximately 26 ppm. After infestation, the plates were covered with a matching clear plastic lid that allows moisture to escape. Infested plates were held in an incubator at 22° C. for 72 h before they were examined under a microscope. Insecticidal activity was recorded for each replication as 100% control (all dead) or 0% control (no effect). Results are presented in Table 2.

Insecticidal Test for Sweet Potato Whitefly (*Bemisia tabaci*).

This test was designed to measure the capability of whitefly eggs and/or young nymphs to develop to large nymphs. Cotton seedlings at the growth stage of one or two expanding true leaf were trimmed so that only the first true leaf remained (cotyledon leaves were also removed). The plants were pre-infested with sweet potato whitefly eggs by keeping plants next to the colony-keeping plants for two or three days. The infested plants were carefully checked for presence of similar egg density before use in the insecticidal tests. Master solutions of test compounds at 2000 ppm were prepared in acetone:water (9:1). The 200 ppm spray solutions were then made by diluting 1 mL of the master solution with 9 mL of 0.025% Tween 20 (in water). The test solutions were sprayed with a hand-held Devilbiss sprayer until runoff to both sides of the infested cotton leaves. Four plants (4 replications) were used for each compound. Reference plants (solvent check) were sprayed with 0.025% Tween 20 containing 9% acetone. Treated plants were held in a holding room for 13 or 14 days at approximately 23° C. and 40% RH before evaluation. To evaluate the efficacy of the compounds, the number of live large nymphs in an area of 1 square inch on the lower surface of the treated cotton leaves was counted under a microscope. Insecticidal activity is determined by Corrected % Control using Abbott's correction formula and presented in Table 2:

Corrected % Control=100*$(X-Y)/X$ where

X=No. of live large nymphs on solvent check plants

Y=No. of live large nymphs on treated plants

Compounds that showed high activity (high Corrected % Control) from the above basic screening were further tested in rundown assays using the same procedures with test doses ranging from 0.4 ppm to 50 ppm. The Corrected % Control values from these rundown assays are given in Table 5.

Insecticidal Test for Colorado Potato Beetle (*Leptinotarsa decemlineata*).

Tomato seedlings at the growth stage of three or four expanding leaves were used. Master solutions of test compounds at 2000 ppm were prepared in acetone:water (9:1). The 50 ppm spray solutions were made by diluting 0.5 mL of the master solution with 18.5 mL of 0.025% Tween 20 (in water). The test solutions were sprayed with a hand-held Devilbiss sprayer until runoff to all surfaces of the plants. Four plants (4 replications) were used for each treatment. Reference plants (solvent check) were sprayed with 0.025% Tween 20 containing 2.25% acetone. Treated plants were held in the laboratory for approximately 3 h to allow drying before the upper portion (with two or three leaves) of a plant was cut and placed in a 10×2.5-cm petri dish containing approximately 10 mL of solidified 1% agar at the bottom. Five $2^{nd}$ or $3^{rd}$ instar larvae were placed on the treated plant tissue, and the petri dishes were covered and held in an incubator at 25° C. At 5 days following treatment, insecticidal activity was evaluated by counting the number of live larvae in each dish. Corrected % Control is calculated using Abbott's correction formula and presented in Table 2:

Corrected % Control=100*$(X-Y)/X$ where

X=No. of live larvae on solvent check plants

Y=No. of live larvae on treated plants

Compounds that showed high activity (high Corrected % Control) from the above basic screening were further tested in rundown assays using the same procedures with test doses ranging from 0.78 ppm to 50 ppm. The Corrected % Control values from these rundown assays are given in Table 6.

Insecticide Utility

The compounds of the invention are useful for the control of insects. Therefore, the present invention also is directed to a method for inhibiting an insect which comprises applying to a locus of the insect an insect-inhibiting amount of a compound of formula (I).

The "locus" of insects is a term used herein to refer to the environment in which the insects live or where their eggs are present, including the air surrounding them, the food they eat, or objects which they contact. For example, insects which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the compounds might also be useful to protect textiles, paper, stored grain, seeds, domesticated animals, buildings or human beings by applying an active compound to or near such objects. The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The terms "insect-inactivating amount" are used to describe the amount, which is sufficient to cause a measurable reduction in the treated insect population. Generally an amount in the range from about 1 to about 1000 ppm by weight active compound is used. For example, insects which can be inhibited include, but are not limited to:

Lepidoptera—*Heliothis* spp., *Helicoverpa* spp., *Spodoptera* spp., *Mythimna unipuncta*, *Agrotis ipsilon*, *Earias* spp., *Euxoa auxiliaris*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*

Thysanoptera—*Frankliniella occidentalis*, *Thrips* spp., *Scirtothrips dorsalis*

Isoptera—*Reticulitermes flavipes*, *Coptotermes formosanus*

Orthoptera—*Blattella germanica*, *Blatta orientalis*, *Gryllotalpa* spp.

Diptera—*Liriomyza* spp., *Musca domestica*, *Aedes* spp., *Culex* spp., *Anopheles* spp.

Hymenoptera—*Iridomyrmex humilis*, *Solenopsis* spp., *Monomorium pharaonis*, *Atta* spp., *Pogonomyrmex* spp., *Camponotus* spp.

Siphonaptera—*Ctenophalides* spp., *Pulex irritans*

Acarina—*Tetranychus* spp., *Panonychus* spp., *Eotetranychus carpini*, *Phyllocoptruta oleivora*, *Aculus pelekassi*, *Brevipalpus phoenicis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

The compounds of the present invention (Formula I) are often applied in conjunction with one or more other insecticides or fungicides to obtain control of a wider variety of pests and diseases. When used in conjunction with other insecticides or fungicides, the presently claimed compounds can be formulated with the other insecticides or fungicides, tank mixed with the other insecticides or fungicides, or applied sequentially with the other insecticides or fungicides.

Some of the insecticides that can be employed beneficially in combination with the compounds of the present invention include: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cyclopro-thrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, difluthrin, dimethrin, empenthrin, fenfluthrin, fenpirithrin, fenpropathrin, fenvalerate, esfenvalerate, flucythrinate, fluvalinate, taufluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

We claim:

1. A compound of the formula (I)

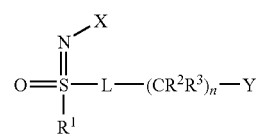

wherein

X represents $NO_2$, CN or $COOR^4$;

$R^1$, S and L taken together represent a 5- or 6-membered ring;

$R^2$ and $R^3$ independently represent hydrogen, methyl, ethyl, fluoro, chloro or bromo;

n is an integer from 0-1;

Y represents hydrogen, $C_1$-$C_4$ alkyl, phenyl, 6-halopyridin-3-yl, 6-($C_1$-$C_4$)alkylpyridin-3-yl, 6-($C_1$-$C_4$)alkoxypyridin-3-yl, 2-chlorothiazol-4-yl, or 3-chloroisoxazol-5-yl; and $R^4$ represents $C_1$-$C_3$ alkyl.

2. A compound of claim 1 in which X represents $NO_2$ or CN.

3. A composition for controlling insects which comprises a compound of any one of claims 1-2 in combination with a phytologically-acceptable carrier.

4. A method of controlling insects which comprises applying to a locus where control is desired an insect-inactivating amount of a compound of any one of claims 1-3.

* * * * *